(12) United States Patent
    Paul et al.

(10) Patent No.: US 10,206,773 B2
(45) Date of Patent: Feb. 19, 2019

(54) ACCOMMODATING INTRAOCULAR LENS AND METHOD OF MANUFACTURE THEREOF

(71) Applicant: ABBOTT MEDICAL OPTICS INC., Santa Ana, CA (US)

(72) Inventors: Marlene L. Paul, Laguna Niguel, CA (US); Michael D. Lowery, Irvine, CA (US); Daniel G. Brady, San Juan Capistrano, CA (US); Arlene Gwon, Newport Beach, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 0 days.

(21) Appl. No.: 15/056,110

(22) Filed: Feb. 29, 2016

(65) Prior Publication Data
    US 2016/0175092 A1     Jun. 23, 2016

Related U.S. Application Data

(60) Division of application No. 12/658,947, filed on Feb. 16, 2010, now Pat. No. 9,271,830, which is a
(Continued)

(51) Int. Cl.
    *A61F 2/16*        (2006.01)
(52) U.S. Cl.
    CPC .......... *A61F 2/1629* (2013.01); *A61F 2/1613* (2013.01); *A61F 2/1624* (2013.01);
(Continued)

(58) Field of Classification Search
    CPC .... A61F 2/1629; A61F 2/1613; A61F 2/1624; A61F 2002/1682; A61F 2002/16905; A61F 2002/1689
(Continued)

(56) References Cited

U.S. PATENT DOCUMENTS

| 1,483,509 A | 2/1924 | Bugbee |
| 2,129,305 A | 9/1938 | William |

(Continued)

FOREIGN PATENT DOCUMENTS

| AU | 3225789 A1 | 10/1989 |
| CA | 2752743 A1 | 9/2010 |

(Continued)

OTHER PUBLICATIONS

Chauvin-Opsia, Azurite ACL (0459).
(Continued)

*Primary Examiner* — David H Willse
*Assistant Examiner* — Tiffany Shipmon
(74) *Attorney, Agent, or Firm* — Johnson & Johnson Surgical Vision, Inc.

(57) ABSTRACT

An accommodating IOL comprises an optic adapted to focus light toward a retina of an eye, and a movement assembly coupled to the eye to provide effective accommodating movement, preferably axial movement, of the optic. At least a portion of the movement assembly is made from a material that is less stiff and/or more resilient than the material used to make the optic. Optionally, an outer ring or support portion made at least partially from either a relatively stiff material such as the material used in the optic or a relatively resilient material such as the material used in the movement assembly is also provided.

14 Claims, 2 Drawing Sheets

Related U.S. Application Data continuation of application No. 10/314,069, filed on Dec. 5, 2002, now Pat. No. 7,662,180.

(52) U.S. Cl.
CPC ............. *A61F 2002/1682* (2015.04); *A61F 2002/1689* (2013.01); *A61F 2002/16905* (2015.04); *A61F 2230/001* (2013.01); *A61F 2230/0013* (2013.01)

(58) Field of Classification Search
USPC ...................................................... 623/6.37
See application file for complete search history.

(56) References Cited

U.S. PATENT DOCUMENTS

| | | |
|---|---|---|
| 2,274,142 A | 2/1942 | Houchin |
| 2,405,989 A | 8/1946 | Beach |
| 2,511,517 A | 6/1950 | Spiegel |
| 2,834,023 A | 5/1958 | Lieb |
| 3,004,470 A | 10/1961 | Hans |
| 3,031,927 A | 5/1962 | Wesley |
| 3,034,403 A | 5/1962 | Neefe |
| RE25,286 E | 11/1962 | De Carle |
| 3,210,894 A | 10/1965 | Bentley et al. |
| 3,222,432 A | 12/1965 | Grandperret |
| 3,227,507 A | 1/1966 | William |
| 3,305,294 A | 2/1967 | Alvarez |
| 3,339,997 A | 9/1967 | Wesley |
| 3,415,597 A | 12/1968 | Willard |
| 3,420,006 A | 1/1969 | Howard |
| 3,431,327 A | 3/1969 | George |
| 3,482,906 A | 12/1969 | David |
| 3,507,565 A | 4/1970 | Luis et al. |
| 3,542,461 A | 11/1970 | Louis et al. |
| 3,583,790 A | 6/1971 | Baker |
| 3,617,116 A | 11/1971 | Jones |
| 3,632,696 A | 1/1972 | Donald |
| 3,673,616 A | 7/1972 | Fedorov et al. |
| 3,673,816 A | 7/1972 | Kuszaj |
| 3,693,301 A | 9/1972 | Lemaitre |
| 3,711,870 A | 1/1973 | Deitrick |
| 3,718,870 A | 2/1973 | Keller |
| 3,751,138 A | 8/1973 | Humphrey |
| 3,760,045 A | 9/1973 | Thiele et al. |
| 3,794,414 A | 2/1974 | Wesley |
| 3,827,798 A | 8/1974 | Alvarez |
| 3,866,249 A | 2/1975 | Flom |
| 3,906,551 A | 9/1975 | Otter |
| 3,913,148 A | 10/1975 | Potthast |
| 3,922,728 A | 12/1975 | Krasnov |
| 3,925,825 A | 12/1975 | Richards et al. |
| 3,932,148 A | 1/1976 | Krewalk, Sr. |
| 3,996,626 A | 12/1976 | Richards et al. |
| 4,010,496 A | 3/1977 | Neefe |
| 4,014,049 A | 3/1977 | Richards et al. |
| 4,038,088 A | 7/1977 | White et al. |
| 4,041,552 A | 8/1977 | Ganias |
| 4,053,953 A | 10/1977 | Flom et al. |
| 4,055,378 A | 10/1977 | Feneberg et al. |
| 4,056,855 A | 11/1977 | Kelman |
| 4,062,629 A | 12/1977 | Winthrop |
| 4,073,579 A | 2/1978 | Deeg et al. |
| 4,074,368 A | 2/1978 | Levy et al. |
| 4,087,866 A | 5/1978 | Choyce et al. |
| 4,102,567 A | 7/1978 | Cuffe et al. |
| 4,110,848 A | 9/1978 | Jensen |
| 4,118,808 A | 10/1978 | Poler |
| 4,159,546 A | 7/1979 | Shearing |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,163 A | 12/1980 | Galin |
| 4,240,719 A | 12/1980 | Guilino et al. |
| 4,244,060 A | 1/1981 | Hoffer |
| 4,244,597 A | 1/1981 | Dandl |
| 4,251,887 A | 2/1981 | Anis |
| 4,253,199 A | 3/1981 | Banko |
| 4,254,509 A | 3/1981 | Tennant |
| 4,261,065 A | 4/1981 | Tennant |
| 4,274,717 A | 6/1981 | Davenport |
| 4,285,072 A | 8/1981 | Morcher et al. |
| 4,298,994 A | 11/1981 | Clayman |
| 4,304,012 A | 12/1981 | Richard |
| 4,307,945 A | 12/1981 | Kitchen et al. |
| 4,315,336 A | 2/1982 | Poler |
| 4,315,673 A | 2/1982 | Guilino et al. |
| 4,316,293 A | 2/1982 | Bayers |
| 4,326,306 A | 4/1982 | Poler |
| 4,338,005 A | 7/1982 | Cohen |
| 4,340,283 A | 7/1982 | Cohen |
| 4,340,979 A | 7/1982 | Kelman |
| 4,361,913 A | 12/1982 | Streck |
| 4,363,143 A | 12/1982 | Callahan |
| 4,366,582 A | 1/1983 | Faulkner |
| 4,370,760 A | 2/1983 | Kelman |
| 4,373,218 A | 2/1983 | Schachar |
| 4,377,329 A | 3/1983 | Poler |
| 4,377,873 A | 3/1983 | Reichert |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,424,597 A | 1/1984 | Schlegel |
| 4,426,741 A | 1/1984 | Bittner |
| 4,435,856 A | 3/1984 | L'Esperance |
| 4,442,553 A | 4/1984 | Hessburg |
| 4,457,592 A | 7/1984 | Baker |
| 4,463,458 A | 8/1984 | Seidner |
| 4,474,751 A | 10/1984 | Haslam et al. |
| 4,474,752 A | 10/1984 | Haslam et al. |
| 4,474,753 A | 10/1984 | Haslam et al. |
| 4,476,591 A | 10/1984 | Arnott |
| 4,478,822 A | 10/1984 | Haslam et al. |
| 4,503,953 A | 3/1985 | Majewski |
| 4,504,981 A | 3/1985 | Walman |
| 4,504,982 A | 3/1985 | Burk |
| 4,512,040 A | 4/1985 | McClure |
| 4,542,542 A | 9/1985 | Wright |
| 4,551,864 A | 11/1985 | Akhavi |
| 4,560,383 A | 12/1985 | Leiske |
| 4,562,600 A | 1/1986 | Ginsberg et al. |
| 4,573,775 A | 3/1986 | Bayshore |
| 4,573,998 A | 3/1986 | Mazzocco |
| 4,575,877 A | 3/1986 | Herrick |
| 4,575,878 A | 3/1986 | Dubroff |
| 4,576,607 A | 3/1986 | Kelman |
| 4,580,882 A | 4/1986 | Nuchman et al. |
| 4,581,033 A | 4/1986 | Callahan |
| 4,596,578 A | 6/1986 | Kelman |
| 4,601,545 A | 7/1986 | Kern |
| 4,608,050 A | 8/1986 | Wright |
| 4,615,701 A | 10/1986 | Woods |
| 4,617,023 A | 10/1986 | Peyman |
| 4,618,228 A | 10/1986 | Baron et al. |
| 4,618,229 A | 10/1986 | Jacobstein et al. |
| 4,624,669 A | 11/1986 | Grendahl |
| 4,629,460 A | 12/1986 | Dyer |
| 4,636,049 A | 1/1987 | Blaker |
| 4,636,210 A | 1/1987 | Hoffer |
| 4,636,211 A | 1/1987 | Nielsen et al. |
| 4,637,697 A | 1/1987 | Freeman |
| 4,641,934 A | 2/1987 | Freeman |
| 4,642,112 A | 2/1987 | Freeman |
| 4,642,114 A | 2/1987 | Rosa |
| 4,646,720 A | 3/1987 | Peyman et al. |
| 4,648,878 A | 3/1987 | Kelman |
| 4,650,292 A | 3/1987 | Baker et al. |
| 4,655,770 A | 4/1987 | Gupta et al. |
| 4,661,108 A | 4/1987 | Grendahl et al. |
| 4,662,882 A | 5/1987 | Hoffer |
| 4,664,666 A | 5/1987 | Barrett |
| 4,666,444 A | 5/1987 | Pannu |

(56) References Cited

U.S. PATENT DOCUMENTS

| | | | |
|---|---|---|---|
| 4,666,445 A | 5/1987 | Tillay |
| 4,676,792 A | 6/1987 | Praeger |
| 4,676,793 A | 6/1987 | Bechert, II |
| 4,687,484 A | 8/1987 | Kaplan |
| 4,693,572 A | 9/1987 | Tsuetaki et al. |
| 4,693,716 A | 9/1987 | MacKool |
| RE32,525 E | 10/1987 | Pannu |
| 4,702,244 A | 10/1987 | Mazzocco |
| 4,704,016 A | 11/1987 | De Carle |
| 4,710,193 A | 12/1987 | Volk |
| 4,710,194 A | 12/1987 | Kelman |
| 4,711,638 A | 12/1987 | Lindstrom |
| 4,720,286 A | 1/1988 | Bailey et al. |
| 4,725,278 A | 2/1988 | Shearing |
| 4,731,078 A | 3/1988 | Stoy et al. |
| 4,737,322 A | 4/1988 | Bruns et al. |
| 4,752,123 A | 6/1988 | Blaker |
| 4,759,762 A | 7/1988 | Grendahl |
| 4,769,033 A | 9/1988 | Nordan |
| 4,769,035 A | 9/1988 | Kelman |
| 4,780,154 A | 10/1988 | Mori et al. |
| 4,781,718 A | 11/1988 | Lindstrom |
| 4,787,903 A | 11/1988 | Grendahl |
| 4,790,847 A | 12/1988 | Woods |
| 4,808,170 A | 2/1989 | Thornton et al. |
| 4,813,955 A | 3/1989 | Achatz et al. |
| 4,816,030 A | 3/1989 | Robinson |
| 4,816,031 A | 3/1989 | Pfoff |
| 4,816,032 A | 3/1989 | Hetland |
| 4,822,360 A | 4/1989 | Deacon |
| 4,828,558 A | 5/1989 | Kelman |
| 4,830,481 A | 5/1989 | Futhey et al. |
| 4,834,749 A | 5/1989 | Orlosky |
| 4,840,627 A | 6/1989 | Blumenthal |
| 4,842,601 A | 6/1989 | Smith |
| 4,863,463 A | 9/1989 | Tjan |
| 4,865,601 A | 9/1989 | Caldwell et al. |
| 4,878,910 A | 11/1989 | Koziol et al. |
| 4,878,911 A | 11/1989 | Anis |
| 4,880,427 A | 11/1989 | Anis |
| 4,881,804 A | 11/1989 | Cohen |
| 4,883,485 A | 11/1989 | Patel |
| 4,888,012 A | 12/1989 | Horn et al. |
| 4,888,014 A | 12/1989 | Nguyen |
| 4,888,015 A | 12/1989 | Domino |
| 4,888,016 A | 12/1989 | Langerman |
| 4,890,912 A | 1/1990 | Visser |
| 4,890,913 A | 1/1990 | De Carle |
| 4,892,543 A | 1/1990 | Turley |
| 4,898,416 A | 2/1990 | Hubbard et al. |
| 4,898,461 A | 2/1990 | Portney |
| 4,902,293 A | 2/1990 | Feaster |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,929,289 A | 5/1990 | Moriya et al. |
| 4,932,966 A | 6/1990 | Christie et al. |
| 4,932,968 A | 6/1990 | Caldwell et al. |
| 4,932,971 A | 6/1990 | Kelman |
| 4,938,583 A | 7/1990 | Miller |
| 4,946,469 A | 8/1990 | Sarfarazi |
| 4,955,902 A | 9/1990 | Kelman |
| 4,961,746 A | 10/1990 | Lim et al. |
| 4,963,148 A | 10/1990 | Sulc et al. |
| 4,976,534 A | 12/1990 | Miege et al. |
| 4,976,732 A | 12/1990 | Vorosmarthy |
| 4,990,159 A | 2/1991 | Kraff |
| 4,994,058 A | 2/1991 | Raven et al. |
| 4,994,080 A | 2/1991 | Shepard |
| 4,994,082 A | 2/1991 | Richards et al. |
| 4,994,083 A | 2/1991 | Sulc et al. |
| 4,995,880 A | 2/1991 | Galib |
| 4,997,442 A | 3/1991 | Barrett |
| 5,000,559 A | 3/1991 | Takahashi et al. |
| 5,002,382 A | 3/1991 | Seidner |
| 5,002,571 A | 3/1991 | O'Donnell et al. |
| 5,018,504 A | 5/1991 | Terbrugge et al. |
| 5,019,098 A | 5/1991 | Mercier |
| 5,019,099 A | 5/1991 | Nordan |
| 5,026,396 A | 6/1991 | Darin |
| 5,044,742 A | 9/1991 | Cohen |
| 5,047,051 A | 9/1991 | Cumming |
| 5,047,052 A | 9/1991 | Dubroff |
| 5,054,905 A | 10/1991 | Cohen |
| 5,056,908 A | 10/1991 | Cohen |
| 5,066,301 A | 11/1991 | Wiley |
| 5,071,432 A | 12/1991 | Baikoff |
| 5,074,877 A | 12/1991 | Nordan |
| 5,074,942 A | 12/1991 | Kearns et al. |
| 5,078,740 A | 1/1992 | Walman |
| 5,089,024 A | 2/1992 | Christie et al. |
| 5,096,285 A | 3/1992 | Silberman |
| 5,108,429 A | 4/1992 | Wiley |
| 5,112,351 A | 5/1992 | Christie et al. |
| 5,117,306 A | 5/1992 | Cohen |
| 5,123,921 A | 6/1992 | Werblin et al. |
| 5,129,718 A | 7/1992 | Futhey et al. |
| 5,133,748 A | 7/1992 | Feaster |
| 5,133,749 A | 7/1992 | Nordan |
| 5,141,507 A | 8/1992 | Parekh |
| 5,147,397 A | 9/1992 | Christ et al. |
| 5,152,788 A | 10/1992 | Isaacson et al. |
| 5,152,789 A | 10/1992 | Willis |
| 5,158,572 A | 10/1992 | Nielsen |
| 5,166,711 A | 11/1992 | Portney |
| 5,166,712 A | 11/1992 | Portney |
| 5,166,719 A | 11/1992 | Chinzei et al. |
| 5,171,266 A | 12/1992 | Wiley et al. |
| 5,171,267 A | 12/1992 | Ratner et al. |
| 5,171,320 A | 12/1992 | Nishi |
| 5,172,723 A | 12/1992 | Sturgis |
| 5,173,723 A | 12/1992 | Volk |
| 5,180,390 A | 1/1993 | Drews |
| 5,192,317 A | 3/1993 | Kalb |
| 5,192,318 A | 3/1993 | Schneider et al. |
| 5,196,026 A | 3/1993 | Barrett et al. |
| 5,197,981 A | 3/1993 | Southard |
| 5,201,762 A | 4/1993 | Hauber |
| 5,203,788 A | 4/1993 | Wiley |
| 5,213,579 A | 5/1993 | Yamada et al. |
| 5,217,491 A | 6/1993 | Vanderbilt |
| 5,225,858 A | 7/1993 | Portney |
| 5,229,797 A | 7/1993 | Futhey et al. |
| 5,236,452 A | 8/1993 | Nordan |
| 5,236,970 A | 8/1993 | Christ et al. |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,275,624 A | 1/1994 | Hara et al. |
| 5,296,881 A | 3/1994 | Freeman |
| 5,326,347 A | 7/1994 | Cumming |
| 5,336,261 A | 8/1994 | Barrett et al. |
| 5,344,448 A | 9/1994 | Schneider et al. |
| 5,349,394 A | 9/1994 | Freeman et al. |
| 5,354,335 A | 10/1994 | Lipshitz et al. |
| 5,358,520 A | 10/1994 | Patel |
| 5,366,499 A | 11/1994 | Py |
| 5,366,502 A | 11/1994 | Patel |
| 5,376,694 A * | 12/1994 | Christ ................ A61L 27/446 523/113 |
| 5,391,202 A | 2/1995 | Lipshitz et al. |
| 5,405,386 A | 4/1995 | Rheinish et al. |
| 5,408,281 A | 4/1995 | Zhang |
| 5,423,929 A | 6/1995 | Doyle et al. |
| RE34,988 E | 7/1995 | Yang et al. |
| RE34,998 E | 7/1995 | Langerman |
| 5,443,506 A | 8/1995 | Garabet |
| 5,476,445 A | 12/1995 | Baerveldt et al. |
| 5,476,514 A | 12/1995 | Cumming |
| 5,480,428 A | 1/1996 | Fedorov et al. |
| 5,489,301 A | 2/1996 | Barber |

(56) References Cited

U.S. PATENT DOCUMENTS

| | | | |
|---|---|---|---|
| 5,489,302 A | 2/1996 | Skottun |
| 5,494,946 A | 2/1996 | Christ et al. |
| 5,496,366 A | 3/1996 | Cumming |
| 5,503,165 A | 4/1996 | Schachar |
| 5,521,656 A | 5/1996 | Portney |
| 5,522,891 A | 6/1996 | Klaas |
| 5,523,029 A | 6/1996 | Korgel et al. |
| 5,549,760 A | 8/1996 | Becker |
| 5,562,731 A | 10/1996 | Cumming |
| 5,574,518 A | 11/1996 | Mercure |
| 5,578,081 A | 11/1996 | McDonald |
| 5,593,436 A | 1/1997 | Langerman |
| 5,607,472 A | 3/1997 | Thompson |
| 5,608,471 A | 3/1997 | Miller |
| 5,609,630 A | 3/1997 | Crozafon |
| 5,628,795 A | 5/1997 | Langerman |
| 5,628,796 A | 5/1997 | Suzuki |
| 5,628,797 A | 5/1997 | Richer |
| 5,650,837 A | 7/1997 | Roffman et al. |
| 5,652,014 A | 7/1997 | Galin et al. |
| 5,652,638 A | 7/1997 | Roffman et al. |
| 5,653,754 A | 8/1997 | Nakajima et al. |
| 5,657,108 A | 8/1997 | Portney |
| 5,661,195 A | 8/1997 | Christ et al. |
| 5,674,282 A | 10/1997 | Cumming |
| 5,682,223 A | 10/1997 | Menezes et al. |
| 5,684,560 A | 11/1997 | Roffman et al. |
| 5,695,509 A | 12/1997 | El Hage |
| 5,702,440 A | 12/1997 | Portney |
| 5,713,958 A | 2/1998 | Weiser |
| 5,716,403 A | 2/1998 | Tran et al. |
| 5,725,576 A | 3/1998 | Fedorov et al. |
| 5,728,155 A | 3/1998 | Anello et al. |
| 5,760,871 A | 6/1998 | Kosoburd et al. |
| 5,766,244 A | 6/1998 | Binder |
| 5,769,890 A | 6/1998 | McDonald |
| 5,770,125 A | 6/1998 | O'Connor et al. |
| 5,776,191 A | 7/1998 | Mazzocco |
| 5,776,192 A | 7/1998 | McDonald |
| 5,800,533 A | 9/1998 | Eggleston et al. |
| 5,814,103 A | 9/1998 | Lipshitz et al. |
| 5,824,074 A | 10/1998 | Koch |
| 5,843,188 A | 12/1998 | McDonald |
| 5,847,802 A | 12/1998 | Menezes et al. |
| 5,864,378 A | 1/1999 | Portney |
| 5,869,549 A | 2/1999 | Christ et al. |
| RE36,150 E | 3/1999 | Gupta |
| 5,876,441 A | 3/1999 | Shibuya |
| 5,876,442 A | 3/1999 | Lipshitz et al. |
| 5,885,279 A | 3/1999 | Bretton |
| 5,895,422 A | 4/1999 | Hauber |
| 5,898,473 A | 4/1999 | Seidner et al. |
| 5,928,283 A | 7/1999 | Gross et al. |
| 5,929,969 A | 7/1999 | Roffman |
| 5,968,094 A | 10/1999 | Werblin et al. |
| 5,984,962 A | 11/1999 | Anello et al. |
| 6,013,101 A | 1/2000 | Israel |
| 6,015,435 A | 1/2000 | Valunin et al. |
| 6,050,970 A | 4/2000 | Baerveldt |
| 6,051,024 A | 4/2000 | Cumming |
| 6,063,118 A | 5/2000 | Nagamoto |
| 6,083,261 A | 7/2000 | Callahan et al. |
| 6,090,141 A | 7/2000 | Lindstrom |
| 6,096,078 A | 8/2000 | McDonald |
| 6,102,946 A | 8/2000 | Nigam |
| 6,106,553 A | 8/2000 | Feingold |
| 6,106,554 A | 8/2000 | Bretton |
| 6,110,202 A | 8/2000 | Barraquer et al. |
| 6,113,633 A | 9/2000 | Portney |
| 6,117,171 A | 9/2000 | Skottun |
| 6,120,538 A | 9/2000 | Rizzo, III et al. |
| 6,136,026 A | 10/2000 | Israel |
| 6,139,576 A | 10/2000 | Doyle et al. |
| 6,152,958 A | 11/2000 | Nordan |
| 6,162,249 A | 12/2000 | Deacon et al. |
| 6,176,878 B1 | 1/2001 | Gwon et al. |
| 6,186,148 B1 | 2/2001 | Okada |
| 6,197,058 B1 | 3/2001 | Portney |
| 6,197,059 B1 * | 3/2001 | Cumming ............ A61F 2/1629 623/6.39 |
| 6,200,342 B1 | 3/2001 | Tassignon |
| 6,210,005 B1 | 4/2001 | Portney |
| 6,217,612 B1 | 4/2001 | Woods |
| 6,221,105 B1 | 4/2001 | Portney |
| 6,224,628 B1 | 5/2001 | Callahan et al. |
| 6,228,115 B1 | 5/2001 | Hoffmann et al. |
| 6,231,603 B1 * | 5/2001 | Lang .................... A61F 2/1613 623/6.24 |
| 6,238,433 B1 | 5/2001 | Portney |
| 6,241,777 B1 | 6/2001 | Kellan |
| 6,251,312 B1 | 6/2001 | Phan et al. |
| 6,258,123 B1 | 7/2001 | Young et al. |
| 6,261,321 B1 | 7/2001 | Kellan |
| 6,277,146 B1 | 8/2001 | Peyman et al. |
| 6,277,147 B1 | 8/2001 | Christ et al. |
| 6,280,471 B1 | 8/2001 | Peyman et al. |
| 6,299,641 B1 | 10/2001 | Woods |
| 6,302,911 B1 | 10/2001 | Hanna |
| 6,322,213 B1 | 11/2001 | Altieri et al. |
| 6,322,589 B1 | 11/2001 | Cumming |
| 6,327,772 B1 | 12/2001 | Zadno-Azizi et al. |
| 6,342,073 B1 | 1/2002 | Cumming et al. |
| 6,358,280 B1 | 3/2002 | Herrick |
| 6,364,906 B1 | 4/2002 | Baikoff et al. |
| 6,387,126 B1 | 5/2002 | Cumming |
| 6,399,734 B1 | 6/2002 | Hodd et al. |
| 6,406,494 B1 | 6/2002 | Laguette et al. |
| 6,423,094 B1 | 7/2002 | Sarfarazi |
| 6,425,917 B1 | 7/2002 | Blake |
| 6,443,985 B1 | 9/2002 | Woods |
| 6,450,642 B1 | 9/2002 | Jethmalani et al. |
| 6,454,802 B1 | 9/2002 | Bretton et al. |
| 6,457,826 B1 | 10/2002 | Lett |
| 6,464,725 B2 | 10/2002 | Skottun et al. |
| 6,468,306 B1 | 10/2002 | Paul et al. |
| 6,474,814 B1 | 11/2002 | Griffin |
| 6,475,240 B1 | 11/2002 | Paul |
| 6,478,821 B1 | 11/2002 | Laguette et al. |
| 6,485,516 B2 | 11/2002 | Boehm |
| 6,488,708 B2 | 12/2002 | Sarfarazi |
| 6,494,911 B2 | 12/2002 | Cumming |
| 6,503,276 B2 | 1/2003 | Lang et al. |
| 6,517,577 B1 | 2/2003 | Callahan et al. |
| 6,524,340 B2 | 2/2003 | Israel |
| 6,533,813 B1 | 3/2003 | Lin et al. |
| 6,533,814 B1 | 3/2003 | Jansen |
| 6,536,899 B1 | 3/2003 | Fiala |
| 6,547,822 B1 | 4/2003 | Lang |
| 6,551,354 B1 | 4/2003 | Ghazizadeh et al. |
| 6,554,859 B1 | 4/2003 | Lang et al. |
| 6,558,420 B2 | 5/2003 | Green |
| 6,559,317 B2 | 5/2003 | Hupperts et al. |
| 6,589,550 B1 | 7/2003 | Hodd et al. |
| 6,592,621 B1 | 7/2003 | Domino |
| 6,598,606 B2 | 7/2003 | Terwee et al. |
| 6,599,317 B1 | 7/2003 | Weinschenk, III |
| 6,609,793 B2 | 8/2003 | Norrby et al. |
| 6,616,691 B1 | 9/2003 | Tran |
| 6,616,692 B1 | 9/2003 | Glick et al. |
| 6,616,693 B1 | 9/2003 | Nguyen |
| 6,638,305 B2 | 10/2003 | Laguette |
| 6,638,306 B2 | 10/2003 | Cumming |
| 6,645,246 B1 * | 11/2003 | Weinschenk, III ... A61F 2/1613 623/6.13 |
| 6,660,035 B1 | 12/2003 | Lang et al. |
| 6,685,315 B1 | 2/2004 | De Carle |
| 6,695,881 B2 | 2/2004 | Peng et al. |
| 6,721,104 B2 | 4/2004 | Schachar et al. |
| 6,730,123 B1 | 5/2004 | Klopotek |
| 6,749,633 B1 | 6/2004 | Lorenzo et al. |
| 6,749,634 B2 | 6/2004 | Hanna |
| 6,761,737 B2 | 7/2004 | Zadno-Azizi et al. |
| 6,764,511 B2 | 7/2004 | Zadno-Azizi et al. |
| 6,767,363 B1 | 7/2004 | Bandhauer et al. |

(56) References Cited

U.S. PATENT DOCUMENTS

| | | |
|---|---|---|
| 6,786,934 B2 | 9/2004 | Zadno-Azizi et al. |
| 6,818,017 B1 | 11/2004 | Shu |
| 6,818,158 B2 | 11/2004 | Pham et al. |
| 6,827,738 B2 | 12/2004 | Willis et al. |
| 6,836,374 B2 | 12/2004 | Esch et al. |
| 6,846,326 B2 | 1/2005 | Zadno-Azizi et al. |
| 6,855,164 B2 | 2/2005 | Glazier |
| 6,858,040 B2 | 2/2005 | Nguyen et al. |
| 6,884,261 B2 | 4/2005 | Zadno-Azizi |
| 6,884,262 B2 | 4/2005 | Brady et al. |
| 6,884,263 B2 | 4/2005 | Valyunin et al. |
| 6,899,732 B2 | 5/2005 | Zadno-Azizi |
| 6,926,736 B2 | 8/2005 | Peng et al. |
| 6,930,838 B2 | 8/2005 | Schachar |
| 6,932,839 B1 | 8/2005 | Kamerling et al. |
| 6,942,695 B1 | 9/2005 | Chapoy et al. |
| 6,966,649 B2 | 11/2005 | Shadduck |
| 7,018,409 B2 | 3/2006 | Glick et al. |
| 7,021,760 B2 | 4/2006 | Newman |
| 7,025,783 B2 | 4/2006 | Brady et al. |
| 7,041,134 B2 | 5/2006 | Nguyen et al. |
| 7,073,906 B1 | 7/2006 | Portney |
| 7,087,080 B2 | 8/2006 | Zadno-Azizi et al. |
| 7,097,660 B2 | 8/2006 | Portney |
| 7,118,596 B2 | 10/2006 | Zadno-Azizi et al. |
| 7,118,597 B2 | 10/2006 | Miller et al. |
| 7,122,053 B2 | 10/2006 | Esch |
| 7,125,422 B2 | 10/2006 | Woods et al. |
| 7,150,759 B2 | 12/2006 | Paul et al. |
| 7,179,292 B2 | 2/2007 | Worst et al. |
| 7,182,780 B2 | 2/2007 | Terwee et al. |
| 7,186,266 B2 | 3/2007 | Peyman |
| 7,188,949 B2 | 3/2007 | Bandhauer et al. |
| 7,198,640 B2 | 4/2007 | Nguyen |
| 7,217,288 B2 | 5/2007 | Esch et al. |
| 7,220,279 B2 | 5/2007 | Nun |
| 7,223,288 B2 | 5/2007 | Zhang et al. |
| 7,226,478 B2 | 6/2007 | Ting et al. |
| 7,238,201 B2 | 7/2007 | Portney et al. |
| 7,247,168 B2 | 7/2007 | Esch et al. |
| 7,261,737 B2 | 8/2007 | Esch et al. |
| 7,344,617 B2 | 3/2008 | Dubrow |
| 7,452,362 B2 | 11/2008 | Zadno-Azizi et al. |
| 7,452,378 B2 | 11/2008 | Zadno-Azizi et al. |
| 7,503,938 B2 | 3/2009 | Phillips |
| 7,615,056 B2 | 11/2009 | Ayton et al. |
| 7,645,300 B2 | 1/2010 | Tsai |
| 7,662,180 B2 | 2/2010 | Paul et al. |
| 7,744,603 B2 | 6/2010 | Zadno-Azizi et al. |
| 7,744,646 B2 | 6/2010 | Zadno-Azizi et al. |
| 7,815,678 B2 | 10/2010 | Ben Nun |
| 7,922,326 B2 | 4/2011 | Bandhauer et al. |
| 8,034,108 B2 | 10/2011 | Bumbalough |
| 8,052,752 B2 | 11/2011 | Woods et al. |
| 8,343,217 B2 | 1/2013 | Bumbalough |
| 9,198,752 B2 | 12/2015 | Woods |
| 9,277,987 B2 | 3/2016 | Smiley et al. |
| 9,364,318 B2 | 6/2016 | Beer |
| 9,433,498 B2 | 9/2016 | Masket et al. |
| 2001/0001836 A1 | 5/2001 | Cumming |
| 2001/0004708 A1 | 6/2001 | Nagai |
| 2001/0012964 A1 | 8/2001 | Lang et al. |
| 2001/0016771 A1 | 8/2001 | Cumming |
| 2001/0018612 A1 | 8/2001 | Carson et al. |
| 2001/0039451 A1 | 11/2001 | Barnett |
| 2001/0044657 A1 | 11/2001 | Kellan |
| 2002/0002404 A1 | 1/2002 | Sarfarazi |
| 2002/0004682 A1 | 1/2002 | Zhou et al. |
| 2002/0011167 A1 | 1/2002 | Figov et al. |
| 2002/0045937 A1 | 4/2002 | Sarfarazi |
| 2002/0068971 A1 | 6/2002 | Cumming |
| 2002/0072795 A1 | 6/2002 | Green |
| 2002/0072796 A1 | 6/2002 | Hoffmann |
| 2002/0095212 A1 | 7/2002 | Boehm |
| 2002/0103536 A1* | 8/2002 | Landreville ........... A61F 2/1629 623/6.37 |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0120329 A1 | 8/2002 | Lang et al. |
| 2002/0138140 A1 | 9/2002 | Hanna |
| 2002/0143395 A1 | 10/2002 | Skottun et al. |
| 2002/0151973 A1 | 10/2002 | Arita et al. |
| 2002/0161434 A1 | 10/2002 | Laguette et al. |
| 2002/0188351 A1 | 12/2002 | Laguette |
| 2002/0193876 A1 | 12/2002 | Lang et al. |
| 2003/0002404 A1 | 1/2003 | Maekawa |
| 2003/0004569 A1 | 1/2003 | Haefliger |
| 2003/0013073 A1 | 1/2003 | Duncan et al. |
| 2003/0018384 A1 | 1/2003 | Valyunin et al. |
| 2003/0020425 A1 | 1/2003 | Ricotti |
| 2003/0033013 A1 | 2/2003 | Callahan et al. |
| 2003/0045933 A1 | 3/2003 | Brady |
| 2003/0050695 A1 | 3/2003 | Lin et al. |
| 2003/0050696 A1 | 3/2003 | Cumming |
| 2003/0050697 A1 | 3/2003 | Paul |
| 2003/0060878 A1 | 3/2003 | Shadduck |
| 2003/0060881 A1 | 3/2003 | Glick et al. |
| 2003/0074060 A1 | 4/2003 | Zadno-Azizi et al. |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0086057 A1 | 5/2003 | Cleveland |
| 2003/0093149 A1 | 5/2003 | Glazier |
| 2003/0105522 A1 | 6/2003 | Glazier |
| 2003/0109925 A1 | 6/2003 | Ghazizadeh et al. |
| 2003/0109926 A1 | 6/2003 | Portney |
| 2003/0114927 A1* | 6/2003 | Nagamoto ............ A61F 2/1613 623/6.37 |
| 2003/0130732 A1 | 7/2003 | Sarfarazi |
| 2003/0135272 A1 | 7/2003 | Brady et al. |
| 2003/0149480 A1 | 8/2003 | Shadduck |
| 2003/0158599 A1 | 8/2003 | Brady et al. |
| 2003/0187504 A1 | 10/2003 | Weinschenk et al. |
| 2003/0187505 A1 | 10/2003 | Liao |
| 2003/0204254 A1 | 10/2003 | Peng et al. |
| 2003/0204255 A1 | 10/2003 | Peng et al. |
| 2004/0002757 A1 | 1/2004 | Lai et al. |
| 2004/0010496 A1 | 1/2004 | Behrendt et al. |
| 2004/0014049 A1 | 1/2004 | Cowsert et al. |
| 2004/0015235 A1 | 1/2004 | Worst et al. |
| 2004/0015236 A1 | 1/2004 | Sarfarazi |
| 2004/0034415 A1 | 2/2004 | Terwee et al. |
| 2004/0039446 A1 | 2/2004 | McNicholas |
| 2004/0054408 A1 | 3/2004 | Glick et al. |
| 2004/0082993 A1 | 4/2004 | Woods |
| 2004/0082994 A1 | 4/2004 | Woods et al. |
| 2004/0082995 A1 | 4/2004 | Woods |
| 2004/0106992 A1 | 6/2004 | Lang et al. |
| 2004/0111151 A1 | 6/2004 | Paul et al. |
| 2004/0111153 A1 | 6/2004 | Woods et al. |
| 2004/0117013 A1 | 6/2004 | Schachar |
| 2004/0148023 A1 | 7/2004 | Shu |
| 2004/0156014 A1 | 8/2004 | Piers et al. |
| 2004/0158322 A1 | 8/2004 | Shen |
| 2004/0162612 A1 | 8/2004 | Portney et al. |
| 2004/0167621 A1 | 8/2004 | Peyman |
| 2004/0181279 A1 | 9/2004 | Nun |
| 2004/0215340 A1 | 10/2004 | Messner et al. |
| 2004/0230299 A1 | 11/2004 | Simpson et al. |
| 2004/0230300 A1 | 11/2004 | Bandhauer et al. |
| 2004/0236422 A1 | 11/2004 | Zhang et al. |
| 2004/0236423 A1 | 11/2004 | Zhang et al. |
| 2004/0249456 A1 | 12/2004 | Cumming |
| 2005/0018504 A1 | 1/2005 | Marinelli et al. |
| 2005/0021139 A1 | 1/2005 | Shadduck |
| 2005/0021140 A1 | 1/2005 | Liao |
| 2005/0027354 A1 | 2/2005 | Brady et al. |
| 2005/0038510 A1 | 2/2005 | Portney et al. |
| 2005/0049700 A1 | 3/2005 | Zadno-Azizi et al. |

(56) References Cited

U.S. PATENT DOCUMENTS

| | | |
|---|---|---|
| 2005/0055092 A1 | 3/2005 | Nguyen et al. |
| 2005/0060032 A1 | 3/2005 | Magnante et al. |
| 2005/0085906 A1 | 4/2005 | Hanna |
| 2005/0085907 A1 | 4/2005 | Hanna |
| 2005/0099597 A1 | 5/2005 | Sandstedt et al. |
| 2005/0113914 A1 | 5/2005 | Miller et al. |
| 2005/0119740 A1 | 6/2005 | Esch et al. |
| 2005/0125056 A1 | 6/2005 | Deacon et al. |
| 2005/0125057 A1 | 6/2005 | Cumming |
| 2005/0125058 A1 | 6/2005 | Cumming et al. |
| 2005/0125059 A1 | 6/2005 | Pinchuk et al. |
| 2005/0131535 A1 | 6/2005 | Woods |
| 2005/0137703 A1 | 6/2005 | Chen |
| 2005/0228401 A1 | 10/2005 | Zadno-Azizi et al. |
| 2005/0234547 A1 | 10/2005 | Nguyen et al. |
| 2005/0246019 A1 | 11/2005 | Blake et al. |
| 2005/0267575 A1 | 12/2005 | Nguyen et al. |
| 2005/0288785 A1 | 12/2005 | Portney et al. |
| 2006/0030938 A1 | 2/2006 | Altmann |
| 2006/0064162 A1 | 3/2006 | Klima |
| 2006/0095127 A1 | 5/2006 | Feingold et al. |
| 2006/0098162 A1 | 5/2006 | Bandhauer et al. |
| 2006/0100702 A1 | 5/2006 | Peyman |
| 2006/0100703 A1 | 5/2006 | Evans et al. |
| 2006/0111776 A1 | 5/2006 | Glick et al. |
| 2006/0116764 A1 | 6/2006 | Simpson |
| 2006/0116765 A1 | 6/2006 | Blake et al. |
| 2006/0149369 A1 | 7/2006 | Cumming et al. |
| 2006/0178741 A1 | 8/2006 | Zadno-Azizi et al. |
| 2006/0184244 A1 | 8/2006 | Nguyen et al. |
| 2006/0209430 A1 | 9/2006 | Spivey |
| 2006/0209431 A1 | 9/2006 | Spivey |
| 2006/0235513 A1 | 10/2006 | Price |
| 2006/0238702 A1 | 10/2006 | Glick et al. |
| 2006/0259139 A1 | 11/2006 | Zadno-Azizi et al. |
| 2006/0271187 A1 | 11/2006 | Zadno-Azizi et al. |
| 2007/0027540 A1 | 2/2007 | Zadno-Azizi et al. |
| 2007/0032866 A1 | 2/2007 | Portney |
| 2007/0050025 A1 | 3/2007 | Nguyen et al. |
| 2007/0067872 A1 | 3/2007 | Mittendorf et al. |
| 2007/0078515 A1 | 4/2007 | Brady |
| 2007/0088433 A1 | 4/2007 | Esch et al. |
| 2007/0100444 A1 | 5/2007 | Brady et al. |
| 2007/0100445 A1 | 5/2007 | Shadduck |
| 2007/0106377 A1 | 5/2007 | Smith et al. |
| 2007/0106379 A1 | 5/2007 | Messner |
| 2007/0106381 A1 | 5/2007 | Blake |
| 2007/0108643 A1 | 5/2007 | Zadno-Azizi et al. |
| 2007/0123591 A1 | 5/2007 | Kuppuswamy et al. |
| 2007/0129798 A1 | 6/2007 | Chawdhary |
| 2007/0135915 A1 | 6/2007 | Klima |
| 2007/0156236 A1 | 7/2007 | Stenger |
| 2007/0213817 A1 | 9/2007 | Esch et al. |
| 2007/0244561 A1 | 10/2007 | Ben Nun |
| 2007/0258143 A1 | 11/2007 | Portney |
| 2007/0260309 A1 | 11/2007 | Richardson |
| 2007/0282247 A1 | 12/2007 | Desai et al. |
| 2007/0299487 A1 | 12/2007 | Shadduck |
| 2008/0004699 A1 | 1/2008 | Ben Nun |
| 2008/0125790 A1 | 5/2008 | Tsai et al. |
| 2008/0140192 A1 | 6/2008 | Humayun et al. |
| 2008/0161913 A1 | 7/2008 | Brady et al. |
| 2008/0161914 A1 | 7/2008 | Brady et al. |
| 2008/0300680 A1 | 12/2008 | Joshua |
| 2009/0012609 A1 | 1/2009 | Geraghty et al. |
| 2009/0234448 A1 | 9/2009 | Weeber et al. |
| 2009/0248152 A1 | 10/2009 | Bumbalough |
| 2009/0248154 A1 | 10/2009 | Dell |
| 2010/0057203 A1 | 3/2010 | Glick et al. |
| 2010/0228346 A1 | 9/2010 | Esch |
| 2011/0035001 A1 | 2/2011 | Woods |
| 2011/0251686 A1 | 10/2011 | Masket |
| 2012/0046744 A1 | 2/2012 | Woods et al. |
| 2015/0173890 A1 | 6/2015 | Portney et al. |
| 2016/0220351 A1 | 8/2016 | Dorronsoro et al. |

FOREIGN PATENT DOCUMENTS

| | | | |
|---|---|---|---|
| CH | 681687 A5 | 5/1993 | |
| DE | 2702117 A1 | 7/1978 | |
| DE | 3246306 A1 | 6/1984 | |
| DE | 4038088 A1 | 6/1992 | |
| DE | 19501444 A1 | 7/1996 | |
| DE | 19951148 A1 | 4/2001 | |
| DE | 20109306 U1 | 8/2001 | |
| DE | 10059482 A1 | 6/2002 | |
| DE | 10125829 A1 | 11/2002 | |
| EP | 64812 A2 | 11/1982 | |
| EP | 162573 A2 | 11/1985 | |
| EP | 212616 A2 | 3/1987 | |
| EP | 246216 A2 | 11/1987 | |
| EP | 328117 A2 | 8/1989 | |
| EP | 329981 A1 | 8/1989 | |
| EP | 331457 A2 | 9/1989 | |
| EP | 336877 A1 | 10/1989 | |
| EP | 0337390 A2 | 10/1989 | |
| EP | 342895 A2 | 11/1989 | |
| EP | 351471 A2 | 1/1990 | |
| EP | 356050 A1 | 2/1990 | |
| EP | 337390 A3 | 5/1990 | |
| EP | 102825 A1 | 12/1990 | |
| EP | 420549 A2 | 4/1991 | |
| EP | 470811 A2 | 2/1992 | |
| EP | 478929 A1 | 4/1992 | |
| EP | 480748 A1 | 4/1992 | |
| EP | 488835 A1 | 6/1992 | |
| EP | 492126 A2 | 7/1992 | |
| EP | 507292 A1 | 10/1992 | |
| EP | 566170 A1 | 10/1993 | |
| EP | 601845 A1 | 6/1994 | |
| EP | 605841 A1 | 7/1994 | |
| EP | 691109 A1 | 1/1996 | |
| EP | 766540 A1 | 4/1997 | |
| EP | 779063 A1 | 6/1997 | |
| EP | 780718 A1 | 6/1997 | |
| EP | 0891102 A3 | 2/1999 | |
| EP | 0897702 * | 2/1999 | ............... A61F 2/16 |
| EP | 897702 A2 | 2/1999 | |
| EP | 766540 B1 | 8/1999 | |
| EP | 1108402 A2 | 6/2001 | |
| EP | 1321112 A1 | 6/2003 | |
| EP | 1424049 A1 | 6/2004 | |
| EP | 1647241 A2 | 4/2006 | |
| EP | 1424049 B1 | 6/2009 | |
| EP | 2523632 | 11/2012 | |
| FR | 488835 A | 11/1918 | |
| FR | 2666504 A1 | 3/1992 | |
| FR | 2666735 A1 | 3/1992 | |
| FR | 2681524 A1 | 3/1993 | |
| FR | 2745711 A1 | 9/1997 | |
| FR | 2778093 A1 | 11/1999 | |
| FR | 2784575 A1 | 4/2000 | |
| GB | 939016 A | 10/1963 | |
| GB | 2058391 A | 4/1981 | |
| GB | 2124500 A | 2/1984 | |
| GB | 2129155 A | 5/1984 | |
| GB | 2146791 A | 4/1985 | |
| GB | 2192291 A | 1/1988 | |
| GB | 2215076 A | 9/1989 | |
| JP | 0211134 | 1/1990 | |
| JP | H02126847 A | 5/1990 | |
| JP | H06508279 | 9/1994 | |
| JP | 1005399 A2 | 1/1995 | |
| JP | 1222760 A2 | 8/1995 | |
| JP | H09501856 A | 2/1997 | |
| JP | H09502542 A | 3/1997 | |
| JP | 10000211 A2 | 1/1998 | |
| JP | H11500030 A | 1/1999 | |
| JP | 11047168 A2 | 2/1999 | |
| JP | 2000508588 T2 | 7/2000 | |
| JP | 2003513704 T | 4/2003 | |
| JP | 2003190193 A | 7/2003 | |
| JP | 2003522592 T2 | 7/2003 | |
| JP | 2003525694 A | 9/2003 | |
| RU | 2014038 C1 | 6/1994 | |

(56) References Cited

FOREIGN PATENT DOCUMENTS

| | | |
|---|---|---|
| RU | 2014039 C1 | 6/1994 |
| WO | 8404449 A1 | 11/1984 |
| WO | 8603961 A1 | 7/1986 |
| WO | 8700299 A1 | 1/1987 |
| WO | 8707496 A1 | 12/1987 |
| WO | 8803961 A1 | 6/1988 |
| WO | 8902251 A1 | 3/1989 |
| WO | 8911672 A1 | 11/1989 |
| WO | 8911872 A1 | 12/1989 |
| WO | 9000889 A1 | 2/1990 |
| WO | 9109336 A1 | 6/1991 |
| WO | 9302639 A1 | 2/1993 |
| WO | 9305733 A1 | 4/1993 |
| WO | 9743984 A1 | 8/1994 |
| WO | 9503783 A1 | 2/1995 |
| WO | 9610968 A1 | 4/1996 |
| WO | 9615734 A2 | 5/1996 |
| WO | 9625126 A1 | 8/1996 |
| WO | 9635398 A1 | 11/1996 |
| WO | 9712272 A1 | 4/1997 |
| WO | 9727825 A1 | 8/1997 |
| WO | 9743984 A1 | 11/1997 |
| WO | 9805273 A1 | 2/1998 |
| WO | 9821621 A1 | 5/1998 |
| WO | 9849594 A1 | 11/1998 |
| WO | 9856315 A1 | 12/1998 |
| WO | 9903427 A1 | 1/1999 |
| WO | 9907309 A1 | 2/1999 |
| WO | 9920206 A1 | 4/1999 |
| WO | 9921491 A1 | 5/1999 |
| WO | 9929266 A1 | 6/1999 |
| WO | 0021467 A1 | 4/2000 |
| WO | 0027315 A1 | 5/2000 |
| WO | 0035379 A1 | 6/2000 |
| WO | 0046629 A1 | 8/2000 |
| WO | 0059407 A1 | 10/2000 |
| WO | 0061036 A1 | 10/2000 |
| WO | 0066037 A1 | 11/2000 |
| WO | 0066039 A1 | 11/2000 |
| WO | 0066040 A1 | 11/2000 |
| WO | 0066041 A1 | 11/2000 |
| WO | 0108605 A1 | 2/2001 |
| WO | 0119288 A1 | 3/2001 |
| WO | 0119289 A1 | 3/2001 |
| WO | 0128144 A1 | 4/2001 |
| WO | 0134061 A1 | 5/2001 |
| WO | 0134066 A1 | 5/2001 |
| WO | 0134067 A1 | 5/2001 |
| WO | 0156510 A1 | 8/2001 |
| WO | 0160286 A1 | 8/2001 |
| WO | 0164135 A1 | 9/2001 |
| WO | 0164136 A2 | 9/2001 |
| WO | 0166042 A1 | 9/2001 |
| WO | 0182839 A1 | 11/2001 |
| WO | 0189816 A1 | 11/2001 |
| WO | 0209620 A1 | 2/2002 |
| WO | 0212523 A2 | 2/2002 |
| WO | 0219949 A2 | 3/2002 |
| WO | 02058391 A2 | 7/2002 |
| WO | 02071983 A1 | 9/2002 |
| WO | 02098328 A1 | 12/2002 |
| WO | 03009051 A2 | 1/2003 |
| WO | 03015657 A2 | 2/2003 |
| WO | 03015669 A2 | 2/2003 |
| WO | 03034949 A2 | 5/2003 |
| WO | 03049646 A2 | 6/2003 |
| WO | 03057081 A2 | 7/2003 |
| WO | 03059196 A2 | 7/2003 |
| WO | 03059208 A2 | 7/2003 |
| WO | 03075810 A1 | 9/2003 |
| WO | 03084441 A1 | 10/2003 |
| WO | 03092552 A1 | 11/2003 |
| WO | 04000171 A1 | 12/2003 |
| WO | 04020549 A1 | 3/2004 |
| WO | 04037127 A2 | 5/2004 |
| WO | 04073559 A1 | 9/2004 |
| WO | 05011531 A2 | 2/2005 |
| WO | 05018504 A1 | 3/2005 |
| WO | 2005019871 A2 | 3/2005 |
| WO | 03082147 A3 | 8/2005 |
| WO | 05084587 A2 | 9/2005 |
| WO | 2005115278 A1 | 12/2005 |
| WO | 06025726 A1 | 3/2006 |
| WO | 06118452 A1 | 11/2006 |
| WO | 2007040964 A1 | 4/2007 |
| WO | 2007067872 A2 | 6/2007 |
| WO | 2008077795 A2 | 7/2008 |
| WO | 2008079671 A1 | 7/2008 |
| WO | 2008108524 A1 | 9/2008 |
| WO | 2009021327 A1 | 2/2009 |
| WO | 2010093823 A2 | 8/2010 |
| WO | 2011017322 A1 | 2/2011 |
| ZA | 8808414 A | 7/1989 |

OTHER PUBLICATIONS

Hanita Lenses, Source Ocular Surgery News International, 1 page.
Mediphacos Ltda, Ocular Surgery News International.
Opthalmed Inc., OMAC-260.
Storz Opthalmics Inc., Model L122UV ACL.
Universe IOL Center, Ocular Surgery News International.
Adler-Grinberg D., "Questioning our classical understanding of accommodation and presbyopia," American Journal of Optometry & Physiological Optics, 1986, vol. 63 (7), pp. 571-580.
Altan-Yaycioglu R., et al., "Pseudo-accommodation with Intraocular Lenses Implanted in the Bag," Journal of Refractive Surgery, 2002, vol. 18 (3), pp. 271-275.
Amo Specs Model AC-21B, AMO Classic Series, 1992, 1 page.
Chiron, Clemente Optfit Model SP525, Brochure Translation, Jul. 12, 1998.
Chrion Vision, Nuvita MA20, 1997, 1 page.
Cohen A.L., "Diffractive Bifocal Lens Design," Optometry and Vision Science, 1993, vol. 70 (6), pp. 461-468.
Cohen A.L., "Practical Design of a Bifocal Hologram Contact Lens or Intraocular Lens," Applied Optics, 1992, vol. 31 (19), pp. 3750-3754.
Co-pending U.S. Appl. No. 09/656,661, filed Sep. 7, 2000.
Co-pending U.S. Appl. No. 09/721,072, filed Nov. 22, 2000.
Fechner P.U., et al., "Iris-Claw Lens in Phakic Eyes To Correct Hyperopia: Preliminary Study," Journal of Cataract and Refractive Surgery, 1998, vol. 24 (1), pp. 48-56.
Foldable Intraocular Lens Implants and Small Incision Cataract Surgery, Ohio Valley Eye Physicians, 2004.
Hara T., et al., "Accommodative Intraocular Lens with Spring Action Part 1 Design and Placement in an Excised Animal Eye," Ophthalmic Surgery, 1990, vol. 21 (2), pp. 128-133.
Hecht E., et al., "Optics", 4th Edition, Addison-Wesley Publishing Company, 1979, pp. 188-190.
Holladay J.T., et al., "A Three-Part System for Refining Intraocular Lens Power Calculations," Journal of Cataract and Refractive Surgery, 1988, vol. 14 (1), pp. 17-24.
Holladay J.T., et al., "Analysis of Edge Glare Phenomena in Intraocular Lens Edge Designs," Journal of Cataract and Refractive Surgery, 1999, vol. 25 (6), pp. 748-752.
Jolab Corp., Source Ophthalmology Times, Mar. 15, 1995, 1 page.
Jacobi F.K., et al., "Bilateral Implantation of Asymmetrical Diffractive Multifocal Intraocular Lenses," Archives of Ophthalmology, 1999, vol. 117 (1), pp. 17-23.
Klien S.A., "Understanding the Diffractive Bifocal Contact Lens," Optometry and Vision Science, 1993, vol. 70 (6), pp. 439-460.
Kuchle M., et al., "Implantation of a New Accommodative Posterior Chamber Intraocular Lens," Journal of Retractive Surgery, 2002, vol. 18 (3), pp. 208-216.
Lane S.S., et al., "Polysulfone Intracorneal Lenses," International Ophthalmology Clinics, 1991, vol. 31 (1), pp. 37-46.
Mandell R.B., "Contact Lens Practice", 4th Edition, Charles C. Thomas Publishers, 1988, 11 pages.

(56) References Cited

OTHER PUBLICATIONS

Mandell R.B., et al., "Mathematical Model of the Corneal Contour," 1965, School of Optometry, University of California, Berkeley, pp. 183-197.
Marron J.C., et al., "Higher-order Kinoforms," Computer and Optically Formed Holographic Optics, 1990, vol. 1211, pp. 62-66.
McCarey B.E., et al., "Modeling Glucose Distribution In the Cornea," Current Eye Research, 1990, vol. 9 (11), pp. 1025-1039.
Menezo J.L., et al., "Endothelial Study of Iris-Claw Phakic Lens: Four Year Follow-Up," Journal of Cataract Refractive Surgery, 1998, vol. 24 (8), pp. 1039-1049.
Ramocki J.M., et al., "Foldable Posterior Chamber Intraocular Lens Implantation in the Absence of Capsular and Zonular Support," American Journal of Ophthalmology, 1999, vol. 127 (2), pp. 213-216.
Simonov A.N., et al., "Cubic Optical Elements for an Accommodative Intraocular Lens," Optics Express, 2006, vol. 14 (17), pp. 7757-7775.
Taylor B.N., ed., The International System of Units (SI), 1991, NIST Special Publication 330, 4 pages.
Tetz M., et al., "Evaluating and Defining the Sharpness of Intraocular Lenses: Part 1: Influence of Optic Design on the Growth of the Lens Epithelial Cells in Vitro," Journal of Cataract and Refractive Surgery, 2005, vol. 31 (11), pp. 2172-2179.
Thornton S., "Accommodation in Pseudophakia," in: Percival SPB Color atlas of lens implantation, Chap. 25, St Louis, ed., Mosby, United States, 1991, pp. 159-162.
Video presented by ASCRS Symposium of Cataracts IOL and Refractive Surgery at the ASOA Congress on Ophthalmic Practice Management. Clinical & Surgical Staff Program on Apr. 10-14, 1999 (VHS Tape).
World Optics Inc., Ophthalmology Times, Mar. 15, 1995.

\* cited by examiner

ACCOMMODATING INTRAOCULAR LENS AND METHOD OF MANUFACTURE THEREOF

RELATED APPLICATIONS

This application is a divisional application of, and claims priority to, U.S. patent application Ser. No. 12/658,947, filed Feb. 16, 2010, which is a continuation application of, and claims priority to U.S. patent application Ser. No. 10/314,069, filed Dec. 5, 2002, now U.S. Pat. No. 7,662,180, the entire contents of which are hereby incorporated by reference in their entirety for all purposes as if fully set forth herein.

BACKGROUND OF THE INVENTION

This invention relates to intraocular lenses (IOLs). More particularly, the invention relates to intraocular lenses which provide accommodating movement in the eye.

The human eye is susceptible to numerous disorders and diseases, a number of which attack the crystalline lens. For example, cataracts mar vision through cloudy or opaque discoloration of the lens of the eye, and can result in partial or complete blindness. When this happens, the crystalline lens can be removed and replaced with an intraocular lens, or IOL. A typical IOL comprises an optic body, or lens, adapted to focus light toward the retina of the eye, and one or more fixation members, or haptics, adapted to secure the IOL in a relatively fixed position in a suitable location such as the anterior chamber, iris, or capsular bag of the eye.

The optic and haptics may be formed as an integral unit from a single material, but in recent years the trend has been toward composite IOLs which use different materials for the various components, so that the properties of these components can be separately optimized. Examples of such composite IOLs are shown in Barrett U.S. Pat. No. 4,997,442 and Vanderbilt U.S. Pat. No. 5,217,491, both of which employ relatively flexible materials in the optic portion and more rigid materials in the haptics. The disclosure of each of these patents is incorporated in its entirety herein by reference.

One drawback of conventional IOLs has been that, while they provide suitable correction for normal distance vision, they do not provide effective accommodation, i.e. the ability to refocus the eyes as needed for viewing both near and distant objects. Until fairly recently, the only solution was to wear eyeglasses, but other options are now available. For instance, multifocal IOLs have been designed for providing near, far, and intermediate vision. In addition, IOLs have been provided with movement assemblies which cooperate with the ciliary muscles and/or other structures of the eye to move the optic axially between near and far vision positions. Examples of this latter class of IOLs, referred to broadly as accommodating IOLs, can be found in Levy U.S. Pat. No. 4,409,691, Cumming U.S. Pat. Nos. 5,674,282 and 5,496,366, Gwon et al. U.S. Pat. No. 6,176,878, Lang et al. U.S. Pat. No. 6,231,603, and Laguette et al. U.S. Pat. No. 6,406,494. The disclosure of each of these patents is incorporated in its entirety herein by reference.

The aforementioned references are concerned primarily with the geometry and mechanical configuration of various accommodating IOLs, but deal only cursorily, if at all, with material selection and manufacturing issues. Certain general properties of the IOL components such as, for instance, flexibility of the movement assembly, are described as being preferred or desirable, but are not delineated in absolute or relative terms.

It is an object of this invention, accordingly, to design an accommodating IOL from an appropriate combination of materials which provide optimum optical qualities, increased accommodation ability, and, preferably, sufficient flexibility to allow the IOL to be inserted through a small incision in an eye.

A further object of the invention is to provide methods for manufacturing the IOLs.

SUMMARY OF THE INVENTION

The present invention provides new and enhanced accommodating intraocular lenses (IOLs). Methods of manufacturing these enhanced IOLs are also disclosed.

In accordance with one aspect of the invention, an accommodating IOL comprises an optic portion, e.g. lens body, adapted to focus light toward a retina of an eye, and a movement assembly coupled to the optic portion or optic and effective, in cooperation with the eye, to provide effective accommodating movement, preferably axial movement, of the optic. At least a portion of the movement assembly is made from a material that is less stiff than the material used to make the optic. Preferably, both materials are polymeric materials.

The term "stiffness", as used herein, shall be understood to relate to the amount of elastic deformation a material undergoes when subjected to a given amount of force. The less elastic deformation a material undergoes per unit force, the stiffer the material. In other words, if two elastic materials are subjected to the same amount of force over the same period of time, the stiffer material is the one which deforms the least. The stiffness of an elastic material, typically expressed in terms of its Young's Modulus, is the opposite of its flexibility; a material which is stiffer than another material is less flexible than that material, and vice versa.

Without wishing to be limited to any particular theory of operation, it is believed that the use of a comparatively flexible material in the movement assembly allows the relatively small forces exerted on the IOL by the zonules, ciliary muscles, and capsular bag of the eye to be translated into increased axial movement of the optic body relative to a substantially identical IOL having a movement assembly made of a comparatively stiff material. In order to provide effective accommodation for a typical presbyopic patient, this axial movement is preferably at least 0.5 mm, and more preferably, in the range of about 1.0 to about 2.5 mm.

The movement assembly may have any suitable configuration effective to cooperate with the eye to provide for effective accommodating movement of the optic, as desired. For example, the movement assembly may comprise a plurality of plate-type members, a single disk-type member, a combination of plate-type members and an outer ring, and the like. The movement assembly may include a hinge assembly. Either the hinge assembly alone or the entire movement assembly may be formed of the less stiff material.

In one example according to the first aspect, the first and second materials both belong to the same class of polymeric materials and are derived from monomers which are mutually compatible, allowing the materials to be co-cured and/or bonded, for example chemically bonded, to one another. For instance, both materials may be acrylic polymeric materials. More specifically, the first material may be an acrylic material that, preferably, is flexible enough to be folded but stiff enough to maintain acceptable image quality. Even more specifically, the first material may be a cross-linked acrylic material, such as a material formed of copolymers of methacrylate and acrylate esters cross-linked with one or more functional acrylate/methacrylate cross-linking components. The second material may be a relatively high water content acrylic polymer in the form of a hydrogel such as, for instance, a hydroxyethyl methacrylate (HEMA) polymer or a methyl methacrylate/N-vinyl pyrrolidone (MMA/NVP) copolymer or the like.

In another example according to the first aspect, both materials may be silicon-containing polymeric materials. Preferably, the first material is a silicon-containing polymeric material including a reinforcing component, such as a silica-reinforcing agent, and the second, less stiff, material is a silicon-containing polymeric material having no reinforcing component, or a reduced amount of reinforcing component than the first material. Except for the amount of the reinforcing component, the second material may have the same formulation as the first material.

In still another example of the first aspect, the first material may be an acrylic polymeric material and the second material may be a silicon-containing polymeric material. More specifically, the first material may be a cross-linked acrylic material, such as a material formed of copolymers of methacrylate and acrylate esters cross-linked with one or more functional acrylate/methacrylate cross-linking components. The second, less stiff, material may be a silicon-containing polymeric material including a reinforcing component, such as a silica-reinforcing agent.

In accordance with a second aspect of the invention, an accommodating IOL comprises an optic portion, e.g. lens body, adapted to focus light toward a retina of an eye, and a movement assembly coupled to the optic portion or optic and effective, in cooperation with the eye, to provide effective accommodating movement, preferably axial movement, of the optic. At least a portion of the movement assembly is made from a material that is more resilient, or responsive, than the material used to make the optic. Preferably, both materials are polymeric materials.

For the purposes of this invention, the terms "resilient" and "responsive" are generally synonymous, and shall be understood to relate to the amount of time an elastic material takes to return to its original state after deformation. A material that returns relatively quickly to its original state is referred to here as a "resilient" or "responsive" material, and a material that takes longer to return to its original state is referred to as "less resilient", "less responsive", "relatively non-resilient", or "relatively non-responsive". Many of the materials referred to herein as "resilient" are also flexible; however, some resilient materials, such as polymethyl methacrylate (PMMA) are relatively stiff.

Without wishing to be limited to any particular theory of operation, it is believed that the use of a comparatively resilient material in the movement assembly allows more rapid accommodation or movement, specifically axial movement, relative to a substantially identical IOL having a movement assembly made entirely of a less resilient material. The increased speed of accommodation means that a patient provided with an enhanced accommodating IOL according to the present invention will be able to refocus relatively quickly when shifting from far to near vision and back again.

The movement assembly may have any suitable configuration effective to cooperate with the eye to provide for effective accommodating movement of the optic, as desired. For example, the movement assembly may comprise a plurality of plate-type members, a single disk-type member, a combination of plate-type members and an outer ring, and the like. The movement assembly may include a hinge assembly. Either the hinge assembly alone or the entire movement assembly may be formed of the more resilient material.

In one example according to the second aspect, the optic may made of a first acrylic material having no water content or a relatively low water content, and at least a portion of the movement assembly may made of a second acrylic material having a higher water content. The higher water content of the second acrylic material makes it more resilient, or responsive, than the second acrylic material. Specifically, the first acrylic material may be a cross-linked acrylic material, such as a material formed of copolymers of methacrylate and acrylate esters cross-linked with one or more functional polyacrylate/methacrylate cross-linking components. The second material may be a relatively high water content acrylic polymer in the form of a hydrogel such as, for instance, a hydroxyethyl methacrylate (HEMA) polymer or a methyl methacrylate/N-vinyl pyrrolidone (MMA/NVP) polymer and the like.

In another example according to the second aspect, the first material may be an acrylic polymeric material and the second material may be a silicon-containing polymeric material. More specifically, the first material may be a cross-linked acrylic material, such as a material formed of copolymers of methacrylate and acrylate esters cross-linked with one or more functional acrylate/methacrylate cross-linking components. The second material may be a silicon-containing polymeric material including a reinforcing component, such as a silica-reinforcing agent.

The movement assemblies of the IOLs in any of the above examples, according to both aspects of the invention, may optionally include a distal end portion or support ring that is made from either a relatively stiff material, such as a material that is the same or similar to the material used in the optic, or a relatively resilient material, such as material that is the same or similar to the material used in the other portion or portions of the movement assembly. Alternatively, the distal end portion or support ring of the movement assembly may be made from a material is both stiff and resilient, such as polymethyl methacrylate (PMMA).

In a first method of manufacturing according to the present invention, an accommodating IOL is produced by shaping a composite member into an optic adapted to focus light toward a retina of an eye, and a movement assembly coupled to the optic and adapted to cooperate with the eye to provide effective accommodating movement of the optic. The composite member includes a central region, which ultimately becomes at least a portion of the optic of the IOL and is made of a first material, and a peripheral region, which ultimately becomes at least a portion of the movement assembly and is made of a second material that is less stiff than the first material.

The step of shaping the composite member is preferably preceded by a step of producing the composite member. In one embodiment, the composite member is produced by polymerizing a first monomeric component to obtain the first material, and polymerizing a second component to obtain the second material.

In a second method of manufacturing according to the present invention, an accommodating IOL is produced by shaping a composite member into an optic adapted to focus light toward a retina of an eye, and a movement assembly coupled to the optic and adapted to cooperate with the eye to provide effective accommodating movement of the optic. The composite member includes a central region, which ultimately becomes at least a portion of the optic of the IOL and is made of a first material, and a peripheral region, which ultimately becomes at least a portion of the movement assembly and is made of a second material that is more resilient than the first material.

The step of shaping the composite member is preferably preceded by a step of producing the composite member. In one embodiment, the composite member is produced by polymerizing a first monomeric component to obtain the first material, and polymerizing a second component to obtain the second material In either of these methods, if the first and second materials have compatible monomeric components, the materials can be co-cast and co-cured and/or bonded, for example, chemically bonded. If the first and second materials do not have compatible monomeric components, the second material is preferably insert molded around the first material.

The composite member may be in the form of a rod, button, or sheet which may be machined, lathed, milled, or the like to form the optic and movement assembly.

Each and every feature described herein, and each and every combination of two or more of such features, is included within the scope of the present invention provided that the features included in such a combination are not mutually inconsistent.

Additional aspects and advantages of the present invention are set forth in the following description and claims, particularly when considered in conjunction with the accompanying drawings in which like parts bear like reference numerals.

DETAILED DESCRIPTION OF THE DRAWINGS

Figure 1:
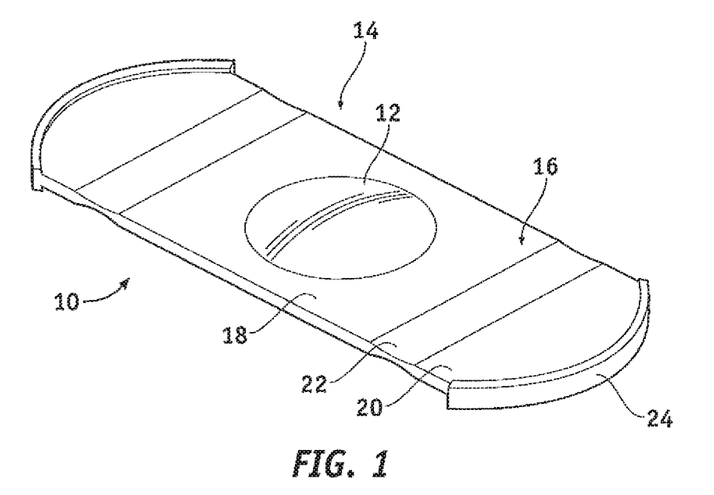
FIG. 1 is a top side view, in perspective, of an IOL in accordance with the present invention.

Referring now to FIG. 1, an accommodating IOL according to the present invention, shown generally at 10, includes a lens body or optic 12. A generally rectangular movement assembly 14 is provided for positioning the optic 12 within the capsular bag of an eye, and for cooperating with the eye to provide accommodating movement of the optic 12. The movement assembly 14 comprises a pair of plate members 16 extending from diametrically opposite edges of the optic 12. The plate members 16 are generally conventional in configuration and may be similar in structure to any of the accommodating plate haptics shown in Cumming U.S. Pat. No. 5,674,282.

The optic 12 is preferably formed of a material having an appropriate balance of superior optical characteristics, flexibility, elasticity, elastic memory and tensile strength. One preferred material meeting these requirements is that acrylic material from which the optic of an IOL marketed under the trademark SENSAR® by Advanced Medical Optics of Santa Ana, Calif. is made. Specifically, the SENSAR® brand of IOL is made of a cross-linked acrylic material formed of copolymers of methacrylate and acrylate esters, cross-linked with a diacrylate ester to produce a cross-linked acrylic copolymer. Useful cross-linked acrylic materials are disclosed in Gupta U.S. Reissue Pat. No. RE #36,150, the disclosure of which is expressly incorporated entirely herein by reference. Such cross-linked acrylic materials have a stiffness, expressed in terms of Young's Modulus, in the range of 1000 to 3000 PSI at body temperature. Typically, the materials disclosed by Gupta return to their original shape (and optical resolution) within about 20 to about 180 seconds after deformation, which, for the purposes of this invention, classifies it as relatively non-responsive or non-resilient.

An alternate preferred material for the optic 12 is a silicon-containing polymeric material identified as SLM-2 and included in IOLs sold by Advanced Medical Optics of Santa Ana, Calif. Specifically, SLM-2 is a crossed-linked siloxane polymer containing 12 to 18 mol percent of aryl siloxane units, and silica reinforcer material in an amount in the range of about 15 to about 45 parts per 100 parts, by weight, of the polymer. This material has a stiffness, as expressed by its Young's Modulus, in the range of at least about 500 to 750 psi. Further details of this material are disclosed in Christ et al. U.S. Pat. Nos. 5,236,970, 5,376,694 and 5,494,946. The disclosure of each of these is incorporated in herein by reference.

Each of the plate members 16 includes a proximal portion 18 joined to the optic 12 and a distal portion 20. Optionally, a hinge 22 may be provided between the proximal portion 18 and the distal portion 20. Also optionally, the distal portion 20 may include a thickened distal end 24 that is contoured to accurately conform to the inner wall of the capsular bag. This thickened distal end 24 is believed to be especially effective in transmitting the forces exerted by the surrounding zonules, ciliary muscle, and capsular bag to the optic 12.

In one embodiment of the invention, each of the plate members 16 is made entirely of a material which is less stiff and/or more resilient than the material used in the optic 12. In another embodiment, the proximal and distal portions 18, 20 of the plate members 16 are made of the same material as the optic 12, while only the hinge 22 is made of a less stiff and/or more resilient material. In yet another embodiment, the thickened distal end 24 is made of a material that is stiffer than the other portions of the plate members 16 and/or is more resilient than the material of the optic 12.

For example, in the case where at least a portion of the optic 12 is made of the material used in making the SENSAR® IOL, at least a portion of the plate members 16 may be formed of an acrylic material having a relatively high water content. Preferably, the water content of the acrylic material is at least about 25%, more preferably at least about 38%. More preferably still, the acrylic material is a hydrophilic hydrogel-forming material selected from the group consisting of poly hydroxyalkyl methacrylates, for example, polyhydroxyethyl methacrylate (poly HEMA) and the like, methyl methacrylate/N-vinyl pyrrolidone-containing copolymers (MMA/NVP copolymers) and mixtures thereof. For instance, either poly HEMA or MMA/NVP may be selected. The MMA/NVP copolymers may be preferred due to potentially lower levels of calcification.

The aforementioned acrylic hydrogels are known to be less stiff (i.e. more flexible) and more resilient than the cross-linked acrylic material of which the SENSAR® brand of IOLs are made. In addition, poly HEMA and MMA/NVP copolymers are derived from monomeric components that are compatible with the monomeric components from which such cross-linked acrylic materials are made.

Because of the compatibility between the monomeric components of the aforementioned acrylic hydrogels and the cross-linked acrylic material, the materials can easily be co-cured with and/or chemically bonded to each other. For instance, in one method of manufacture, the resilient portion of the IOL 10 is formed by polymerizing a precursor material, for instance a hydrogel-forming acrylic precursor material, in a mold. After polymerization, a hole is bored in the acrylic hydrogel-forming material, and a different precursor material, for instance a cross-linked acrylic precursor material, is polymerized in the hole to form a button having a relatively stiff, cross-linked acrylic core surrounded by a less stiff, or more flexible, acrylic hydrogel sheath. The sheath portion of the button is then milled to form the movement assembly 14 and the core is lathed as desired to form the optic 12 of the IOL 10.

Alternatively, the polymer forming the movement assembly is polymerized around a rod having the diameter desired of the optic. The rod is then removed and the polymer forming the optic is polymerized within the resulting space. The IOL is then lathed and milled as in the previous method. Manufacturing processes similar to this and the method outlined above are described in greater detail in Barrett U.S. Pat. No. 4,997,442 and Vanderbilt U.S. Pat. No. 5,217,491, the disclosures of both of which are incorporated by reference herein.

In still another similar method, the different polymers may be co-cast as sections of a sheet, rather than a rod or button.

In the case where the optic 12 is made from a silicon-containing polymeric material, at least a portion of the plate members 16 may be made from a less stiff silicon-containing polymeric material. For instance, if the optic 12 is made from the aforementioned SLM-2 material, at least a portion of the plate haptics 16 could be made from a material having substantially the same formulation as SLM2, but with a reduced amount of the silica-reinforcing agent. Because of the reduction of the silica-reinforcing agent, the plate members 16 are more flexible relative to the optic 12, and are thus able to effect more axial movement of the optic 12 than if the plate members 16 were made of a material having exactly the same formulation as the optic 12.

A one-piece IOL 10 having the optic 12 made from a silicon-containing polymeric material and at least a portion of the movement assembly 14 made from a less stiff silicon-containing polymeric material could be co-molded or insert molded using conventional manufacturing techniques well known in the art.

Yet another embodiment of the IOL 10 includes an optic 12 formed of a relatively stiff foldable acrylic polymeric material such as the aforementioned cross-linked acrylic polymeric material, and at least a portion of the movement assembly made of a less stiff silicon-containing material such as SLM-2. In this case, the more flexible silicon-containing polymeric material is insert molded around the stiffer acrylic polymeric material.

Figure 2:
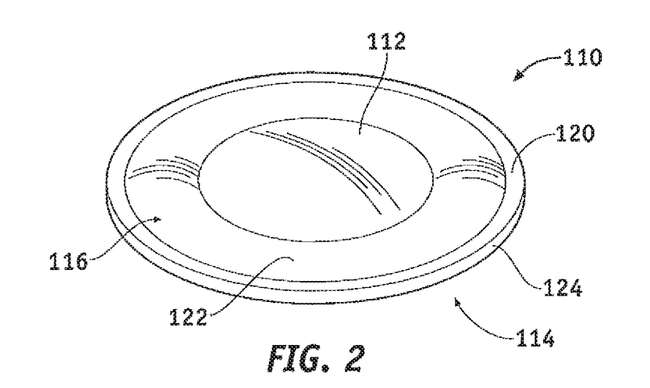
FIG. 2 is a top side view, in perspective, of an IOL in accordance with an alternate embodiment of the invention.

FIG. 2 shows an accommodating IOL 110 according to an alternate embodiment of the invention. Components of IOL 110 which correspond to components of IOL 10 are indicated by the same reference numeral increased by 100.

The IOL 110 comprises an optic 112 circumscribed by a movement assembly 14. The movement assembly 114 comprises a disc member 116 having a springy intermediate portion 122 and a distal portion 120 having a peripheral surface 124. The disc-shaped movement assembly 114 is similar in configuration to movement assemblies shown in Gwon U.S. Pat. No. 6,176,878 and Laguette et al. U.S. Pat. No. 6,406,494.

In one embodiment of the invention, the optic 112 is made from an acrylic polymeric material such as the cross-linked acrylic polymeric material described above in connection with FIG. 1. The intermediate portion 122 of the flexible member 116 is made from a less stiff and more resilient acrylic material such as one of the acrylic hydrogels mentioned above. The distal portion 120 of the flexible member 116 could be formed of the same material as the intermediate portion 122 or a stiffer material, such as the same cross-linked acrylic polymeric material used in the optic 112. Increased stiffness of the distal portion 120 may result in more effective transmission of the forces from the surrounding zonules, ciliary muscle, and capsular bag.

Alternatively, the optic 112 is made from a silicon-containing polymeric material such as the SLM-2 material described above, and at least the intermediate portion 122 of the flexible member is formed of a less stiff silicon-containing material such as one having substantially the same formulation as SLM-2 but with less silica-reinforcing agent. The distal portion 120 of the flexible member 116 could be made of either SLM-2 or the less stiff silicon-containing material.

In yet another alternative, the optic 112 could be made from a relatively stiff acrylic polymeric material such as the previously mentioned cross-linked acrylic polymeric material, and at least a portion of the flexible member 116 could be made of a less stiff silicon-containing polymeric material such as SLM-2.

Figure 3:
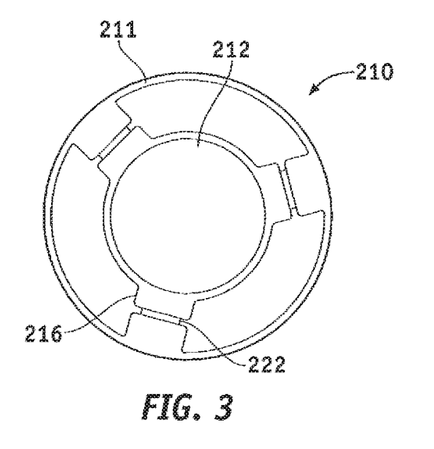
FIG. 3 is a plan view of an IOL in accordance with another alternate embodiment of the invention.

FIG. 3 shows an accommodating IOL 210 according to an especially useful embodiment of the invention. Components of IOL 210 which correspond to IOL 10 are indicated by the same reference numeral increased by 200.

The IOL 210 comprises a circular outer capsular bag support ring 211, an inner optic 212, and a plurality of radially oriented plate-like members 216 extending therebetween. Preferably, the members 216 are arranged 120° apart with substantial voids therebetween and between the optic 212 and the support ring 211. In addition, each member 216 preferably includes a reduced-thickness hinge portion 222.

While the exact configuration of the fixation members 216 is not essential to the invention, and a more solid interface rather than discrete fixation members is also acceptable, the combination of the illustrated tripod configuration, hinge portions 222 and the selection of materials as discussed herein results in particularly effective axial movement of the optic 212. Specifically, the movement assembly of IOL 210 is effective in providing an amount of axial movement in a range of about 0.5 or about 1.5 mm to about 2.0 mm or about 2.5 mm. This amount of movement is sufficient to provide in the range of about 1 to about 2.5 or about 3.5 diopters of accommodation or more, depending on various factors such as the corrective power of the optic 12. Accommodation in this range is sufficient for the majority of presbyopic patients.

As in FIGS. 1 and 2, the optic 212 of the IOL 210 may be formed of an acrylic polymeric material, such as the aforementioned cross-linked acrylic polymeric material, that is stiff enough to provide excellent optical qualities, yet flexible enough to be folded for insertion through a small incision in an eye. At least the hinge portion 222 if not the entirety of each fixation member 216 may be made of a less stiff and more resilient acrylic material, for instance an acrylic hydrogel material such as poly HEMA or MMA/NVP copolymers. The support ring 211 may be made of an acrylic polymeric material having the same or greater stiffness as the optic 212 in order to maximize transmission of forces from the zonules, ciliary muscle, and capsular bag, or it may be made of an acrylic polymeric material having the same or less stiffness than the fixation members 216 in order to maximize the amount of movement obtained from a small amount of force. The acrylic-based materials of this embodiment can easily be co-cured or bonded using manufacturing techniques similar to those discussed in connection with the acrylic-based embodiment of FIG. 1.

Alternatively, the optic 212 of the IOL 210 may be formed of a silicon-containing polymeric material such as SLM-2, and at least the hinge 222 if not the entirety of each fixation member 216 may be formed of a less stiff silicon-containing polymeric material such as one having substantially the formulation as SLM-2 but with a smaller amount of silica-reinforcing agent. The support ring 211 may be made of a silicon-containing polymeric material having the same or greater stiffness as the optic 212, or it may be made of an silicon-containing polymeric material having the same or less stiffness than the fixation members 216. A one-piece IOL 210 having all its components made from silicon-containing polymeric material as in this embodiment could be co-molded or insert molded using conventional manufacturing techniques.

In yet another alternative, the optic 212 could be made from a relatively stiff acrylic polymeric material such as the aforementioned cross-linked acrylic polymeric material, and at least a portion of each fixation member 216 could be made of a less stiff silicon-containing polymeric material such as SLM-2. Insert molding may be the most appropriate manufacturing technique for this combination of materials.

Figure 4:
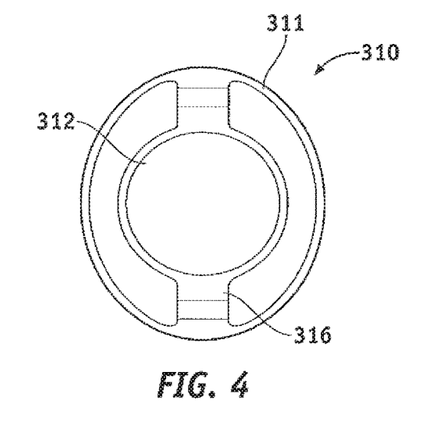
FIG. 4 is a plan view of an IOL in accordance with still another alternate embodiment of the invention.

FIG. 4 shows an IOL 310 according to yet another embodiment of the invention. Components of IOL 310 which correspond to IOL 210 are indicated by the same reference numeral increased by 100.

IOL 310 is substantially similar to IOL 210, except that only two plate-like members 216 are provided, and the support ring 311 is oval rather than circular. As in the foregoing examples, the optic 312 is made of a somewhat stiff yet preferably foldable polymeric material such as cross-linked acrylic polymeric material or SLM-2, while the members 316 are made of less stiff material such as an acrylic hydrogel material or SLM-2 in the first instance, or, in the second instance, a silica-based polymeric material containing a smaller amount of silica-reinforcing agent than SLM-2. The support ring 311 may be of a material that is the same or stiffer than the optic 312, or the same or less stiff than the fixation members 316, depending on the desired result.

Figure 5:
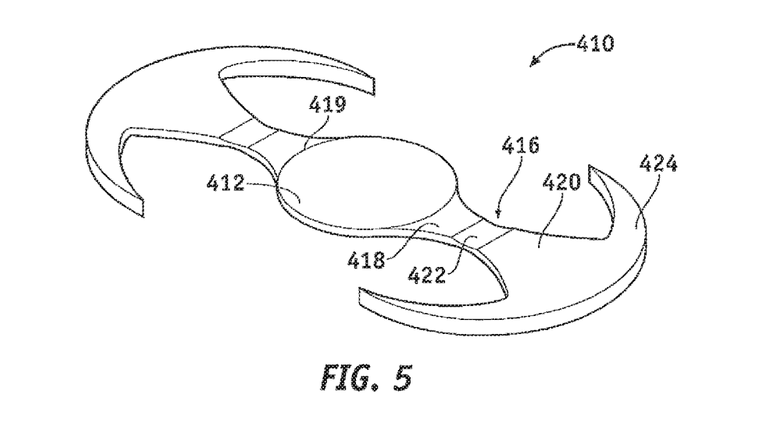
FIG. 5 is a top side view, in perspective, in accordance with yet another embodiment of the invention.

FIG. 5 shows an IOL 410 according to still another embodiment of the invention. Components of IOL 410 which correspond to IOL 10 are indicated by the same reference numeral increased by 400.

IOL 410 comprises an optic 412 and a pair of oppositely extending, generally hour-glass shaped members 416. Each member 416 includes a proximal portion 418 that gradually decreases in width from its proximal end 419 to an intermediate portion 422, and a distal portion 420 that gradually increases in width from the intermediate portion 422 to an enlarged support portion or foot 424. The intermediate portion 422 is preferably reduced in thickness and functions as a hinge. The enlarged support portion or foot 424 of each fixation member 416 is preferably curved in configuration and contoured to generally conform to the inner wall of the capsular bag.

The optic 412 is preferably made of a somewhat stiff yet foldable material such as the previously mentioned cross-linked acrylic polymeric material or SLM2, but can also be made of a stiffer, non-foldable material such as PMMA. At least a portion of each fixation member 416 is made from a material that is less stiff than the optic 412. The support portion or foot 424 of each fixation member 416 is made of a material that is either stiff, resilient, or both, depending on the desired result.

For instance, in one embodiment of the invention, the optic 412 is formed from a relatively stiff acrylic polymer material such as the aforementioned cross-linked acrylic polymeric material, while at least the intermediate portion or hinge 422 of each fixation member 416 is formed from a less stiff acrylic hydrogel material such as poly HEMA or MMA/NVP copolymers. The support portion 424 may be formed at least partially from the same cross-linked acrylic polymeric material as the optic 412, or from an even stiffer but more resilient material such as milled or extruded PMMA. Alternatively, the support portion 424 may be formed of the same acrylic hydrogel material as the hinge 422 or the entirety of each fixation member 416. The components in any of these combinations of materials may be co-molded.

In another embodiment of the invention, the optic 412 is formed of SLM-2, while at least the hinge 422 of each fixation member 416 is formed of a less stiff silicon-containing material, such as a material having substantially the same formulation as SLM-2, but with a smaller amount of silica-reinforcing agent. The support portion 424 may be formed at least partially of the same SLM-2 material as the optic 412, or from a stiffer but more resilient material such as milled or extruded PMMA. Alternatively, the support portion may be formed of the same, less stiff silicon-containing material as the hinge 422 or entirety of each fixation member 416.

In still another embodiment, the optic 412 is made of an acrylic polymeric material such as the aforementioned cross-linked acrylic polymeric material, and at least a portion of each fixation member 416 is made of a less stiff, silicon-based polymeric material such as SLM-2. The support portion 424 may be formed at least partially from the same cross-linked acrylic polymeric material as the optic 412, or from an even stiffer, but more resilient material such as milled or extruded PMMA. Alternatively, the support portion 424 may be formed from the same silicon-based polymeric material as the hinge 422 or the entirety of each fixation member 416. The components in any of these combinations of materials may be insert molded.

In yet another embodiment, the optic 412 is made of PMMA, and the fixation members 416 are made of a more flexible material, for instance an acrylic hydrogel material such as poly HEMA or MMA/NVP copolymers. The support portion 424 of each fixation member 416 may be made at least partially from the same PMMA material as the optic, or the same acrylic hydrogel material as the fixation members 416. The PMMA components of an IOL 410 according to this embodiment may not be foldable for insertion through a small incision, but the loss of this characteristic may be compensated for by increased optical quality and increased resilience, leading to greater axial movement of the optic 412 and better overall accommodation.

While this invention has been described with respect to various specific examples and embodiments, it is to be understood that the invention is not limited thereto and that it can be variously practiced within the scope of the following claims.

What is claimed is:

1. An intraocular lens comprising:
   an optic adapted to focus light toward a retina of an eye, at least a portion of the optic being made of a first material; and
   a movement assembly coupled to the optic and adapted to cooperate with the eye to provide effective accommodating movement of the optic in response to action of the eye, at least a portion of the movement assembly being made of a second material that is more resilient than the first material,
      wherein the movement assembly comprises a pair of opposing fixation members and a pair of opposing enlarged support portions at distal portions of the pair of opposing fixation members, the pair of opposing enlarged support portions adapted to contact a capsular bag of the eye,
      wherein each fixation member of the pair of opposing fixation members decreases in width from a proximal end coupled to the optic to an intermediate portion, and increases in width from the intermediate portion to the distal portion, and
      wherein, for each fixation member, a hinge having a thickness less than the proximal portion and the distal portion is provided at a narrowest section of the intermediate portion.

2. The intraocular lens of claim 1, wherein the first material and the second material include a first polymeric material and a second polymeric material, respectively.

3. The intraocular lens of claim 2, wherein the first and second polymeric materials are derived from monomers which are mutually compatible.

4. The intraocular lens of claim 3, wherein the first polymeric material is chemically bonded to the second polymeric material.

5. The intraocular lens of claim 2, wherein the first and second polymeric materials are both acrylic polymeric materials.

6. The intraocular lens of claim 1, wherein the second material has an increased water content relative to the first material.

7. The intraocular lens of claim 6, wherein the first material comprises a cross-linked acrylic polymer, and the second material comprises an acrylic hydrogel-forming polymer.

8. The intraocular lens of claim 7, wherein the second material comprises a polymer selected from the group consisting of poly hydroxyalkyl methacrylates, methyl methacrylate/N-vinyl pyrrolidone-containing copolymers and mixtures thereof.

9. The intraocular lens of claim 1, wherein the movement assembly at least partially circumscribes the optic.

10. The intraocular lens of claim 1, wherein at least one of the first and second materials is a silicon-containing polymeric material.

11. The intraocular lens of claim 1, wherein each fixation member of the pair of opposing fixation members is hourglass shaped.

12. The intraocular lens of claim 11, wherein each enlarged support portion of the pair of enlarged support portions is crescent-shaped.

13. The intraocular lens of claim 12, wherein each enlarged support portion of the pair of enlarged support portions tapers from a proximal end having a first width at the distal portion of the fixation member to a distal end having a second width less than the first width.

14. The intraocular lens of claim 1, wherein the first material comprises a first silicon-containing polymeric material and the second material comprises a second silicon-containing polymeric material that is less stiff than the first silicon-containing polymeric material.

* * * * *